US006723871B2

(12) United States Patent
Tada et al.

(10) Patent No.: US 6,723,871 B2
(45) Date of Patent: Apr. 20, 2004

(54) PROCESS FOR PRODUCING OPTICALLY ACTIVE ALCOHOL

(75) Inventors: Kenichi Tada, Hiratsuka (JP); Takashi Miura, Hiratsuka (JP)

(73) Assignee: Takasago International Corporation, Tokyo (JP)

(*) Notice: Subject to any disclaimer, the term of this patent is extended or adjusted under 35 U.S.C. 154(b) by 24 days.

(21) Appl. No.: 10/142,983

(22) Filed: May 13, 2002

(65) Prior Publication Data

US 2003/0004362 A1 Jan. 2, 2003

(30) Foreign Application Priority Data

May 18, 2001 (JP) .................................... P. 2001-150012
Mar. 25, 2002 (JP) .................................... P. 2002-082865

(51) Int. Cl.$^7$ .............................................. C07C 69/66
(52) U.S. Cl. ...................................................... 560/184
(58) Field of Search ........................... 560/184; 562/512

(56) References Cited

U.S. PATENT DOCUMENTS

| 4,933,482 A | 6/1990 | Sayo et al. |
| 5,118,836 A | 6/1992 | Tanida et al. |
| 5,716,841 A | 2/1998 | Tixidre et al. |

FOREIGN PATENT DOCUMENTS

| EP | 0 295 109 A1 | 12/1988 |
| EP | 0 577 446 A2 | 1/1994 |
| EP | 0 916 637 A1 | 5/1999 |
| JP | 63-310847 A | 12/1988 |
| JP | 3-151348 A | 6/1991 |
| JP | 3-2544694 A | 11/1991 |
| JP | 5-219986 A | 8/1993 |
| JP | 8-289799 A | 5/1996 |
| JP | 9-268146 A | 10/1997 |
| JP | 10-236986 A | 9/1998 |
| JP | 344694 | 12/2000 |
| JP | 104795 | 4/2001 |

OTHER PUBLICATIONS

Yuzo Komatsu et al., Enzymatic Synthesis of Both Enantiomers 2–Methylene–4–(fluoromethyl)–4–butanolides, J.Org. Chem. 1998, 63, pp. 8058–8061.

Luciano Antolini, Stereoselective Synthesis and Absolute Configuration of (1'R,3R,4R)–4–acetoxy–3–(2',2',2'–trifluoro–1'–hydroxyethyl)–azetidin–2–one, Tetrahedron: Asymmetry 9(1998) pp. 285–292.

Akio Fuji, Ruthenium(II)–Catalyzed Asymmetric Transfer Hydrogenation of Ketones Using a Formic Acid–Triethylamine Mixture, J. Am. Chem. Soc. 1996, 118, pp. 2521–2522.

10–236986, Patent Abstracts of Japan, Sep. 8, 1998.

Japanese Patent Publication 2000344694 dated Dec. 12, 2000.

Japanese Patent Publication 2001104795 dated Apr. 12, 2001.

Primary Examiner—Shailendra Kumar
(74) Attorney, Agent, or Firm—Sughrue Mion, PLLC

(57) ABSTRACT

A novel production process capable of obtaining an optically active alcohol in a high optical purity by subjecting a β-keto ester such as a 3-perfluoroalkyl-3-oxopropionate ester or a 3-trichloroalkyl-3-oxopropionate ester to asymmetric reduction in simple and convenient operations.

7 Claims, No Drawings

PROCESS FOR PRODUCING OPTICALLY ACTIVE ALCOHOL

FIELD OF THE INVENTION

The present invention relates to a practically valuable and novel process for producing an optically active alcohol, which comprises a step of subjecting a β-keto ester to an asymmetric reduction in the presence of an optically active catalyst.

BACKGROUND OF THE INVENTION

Hitherto, the following are known as methods for synthesizing optically active 4,4,4-trifluoro- or 4,4,4-trichloro-3-hydroxybutanoate esters: 1) a method of obtaining an optically active 4,4,4-trifluoro-3-hydroxybutanoate ester by selective enzymatic hydrolysis of the ester group of a 4,4,4-trifluoro-3-hydroxybutanoate ester, which is a racemic mixture, used as a starting material using a lipase and extraction of unhydrolyzed (R)-enantiomer (JP-A-8-289799); 2) a method of obtaining a hydrolyzed (R)-enantiomer by acetylation of the hydroxyl group of a 4,4,4-trifluoro-3-hydroxybutanoate ester, which is a racemic mixture, and successive enzymatic hydrolysis with a lipase (J. Org. Chem., Vol. 63, pp. 8058–8061 (1998)); 3) a method of obtaining an optically active 4,4,4-trifluoro-3-hydroxybutanoate ester by ester exchange through a reaction of an optically active 4,4,4-trifluoro-3-hydroxybutanoate ester with an alcohol in the presence of an ammonium salt of a sulfonic acid derivative (JP-A-3-151348); 4) a method of obtaining an optically active 4,4,4-trifluoro-3-hydroxybutanoate ester or 4,4,4-trichloro-3-hydroxybutanoate ester by reduction of a 4,4,4-trifluoro-3-oxobutanoate ester or 4,4,4-trichloro-3-oxobutanoate ester using baker's yeast (Tetrahedron Asymmetry, Vol. 9, pp. 285–292 (1997)); 5) a method of obtaining an optically active 4,4,4-trifluoro-3-hydroxybutanoate ester by asymmetric ester exchange of a 4,4,4-trifluoro-3-hydroxybutanoate ester, which is a racemic mixture, with a vinyl ester using an enzyme derived from a microorganism or wheat germ (JP-A-5-219986); 6) a method of obtaining an optically active 4,4,4-trifluoro-3-hydroxybutanoate ester by hydrogenation of a 4,4,4-trifluoro-3-oxobutanoate ester in the presence of a nickel catalyst supporting an optically active compound (JP-A-9-268146); 7) a method of obtaining an optically active 4,4,4-trichloro-3-hydroxybutanoate ester by asymmetric hydrogenation of a 4,4,4-trichloro-3-oxobutanoate ester using an optically active BINAP catalyst (JP-A-63-310847); 8) a method of conducting a reaction of a 4,4,4-trifluoro-3-hydroxybutanoate ester, which is a racemic mixture, with acetic anhydride using a lipase to obtain an unreacted 4,4,4-trifluoro-3-hydroxybutanoate ester as an optically active one (JP-A-3-254694); and so forth.

However, in the above synthetic methods of optically active alcohols, the following have been found to be problems: the synthetic methods using enzymes require tedious operations and process controls and have limitations on kinds of reaction substrates, and also alcohols having an absolute configuration are restricted to specific ones; in the case of using a 4,4,4-trifluoro-3-hydroxybutanoate ester, which is a racemic mixture, as a reaction substrate, the yield of optically active 4,4,4-trifluoro-3-hydroxybutanoate ester having a desired configuration is 50% or less; in the case of reducing a 4,4,4-trifluoro-3-oxobutanoate ester or a 4,4,4-trichloro-3-oxobutanoate ester using baker's yeast, the resulting 4,4,4-trifluoro-3-hydroxybutanoate ester or 4,4,4-trichloro-3-hydroxybutanoate ester has a low optical purity; and a 4,4,4-trifluoro-3-hydroxybutanoate ester or 4,4,4-trichloro-3-hydroxybutanoate ester obtainable by asymmetric hydrogenation using a nickel catalyst supporting an optically active compound or an optically active Ru-BINAP catalyst has an insufficient optical purity. In particular, in the fields of medicines and functional materials, it is important to obtain a compound having a specific absolute configuration in a good optical purity, and thus it is necessary to solve the problems in the above methods.

SUMMARY OF THE INVENTION

An object of the invention is to provide a novel production process capable of obtaining an optically active alcohol having a desired absolute configuration in a high optical purity by subjecting a β-keto ester such as a 3-perfluoroalkyl-3-oxopropionate ester or a 3-trichloroalkyl-3-oxopropionate ester to asymmetric reduction in simple and convenient operations.

Under such circumstances, as a result of extensive studies, the present inventors have found that, by subjecting a β-keto ester represented by the general formula (I) such as a 4,4,4-trifluoro-3-oxobutanoate ester or a 4,4,4-trichloro-3-oxobutanoate ester to hydrogen-transfer type asymmetric reduction in the presence of an optically active ruthenium-diamine complex represented by the general formula (II), a corresponding optically active alcohol is obtained in a high optical purity. Based on a result of further examinations, they have accomplished the invention.

Heretofore, the methods of obtaining an optically active hydroxy compound by subjecting a carbonyl compound to asymmetric hydrogen-transfer type reduction using an optically active ruthenium-diamine complex represented by the general formula (II) have been known (JP-A-10-236986, J. Am. Chem. Soc., Vol. 118, pp. 2521–2522 (1996)). However, these methods are a method for producing an optically active alcohol having an acetylene bond by subjecting a carbonyl compound having an acetylene bond to asymmetric hydrogen-transfer type reduction and a method of an optically active hydroxy compound by subjecting a carbonyl compound such as an aryl alkyl ketone to asymmetric hydrogen-transfer type reduction. Although a description of a β-keto acid derivative exists in JP-A-10-236986, there is no concrete example with regard to the compound and also, when an acetoacetate ester as a β-keto acid derivative has been subjected to asymmetric reduction using an optically active ruthenium-diamine complex, no reduction has proceeded. However, the inventors have found that, in the case that a 4,4,4-trifluoro-3-oxobutanoate ester or a 4,4,4-trichloro-3-oxobutanoate ester is subjected to an asymmetric hydrogen-transfer type reduction, a corresponding optically active alcohol is obtained in a high optical purity, and as a result of further extensive examinations, they have accomplished the invention.

Namely, the invention relates to:

(1) a process for producing an optically active alcohol represented by the general formula (III):

(wherein * represents an asymmetric carbon atom, $R^1$ represents a $C_1$–$C_{10}$ linear or branched perfluoroalkyl or perchloroalkyl group and $R^2$ represents a $C_1$–$C_6$ lower alkyl group or benzyl group which may have a substituent), which comprises a step of subjecting a β-keto ester represented by the general formula (I):

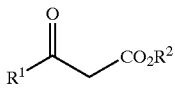

(I)

(wherein $R^1$ and $R^2$ each has the same meaning as described above) to a hydrogen-transfer reaction in the presence of an optically active ruthenium-diamine complex represented by the general formula (II):

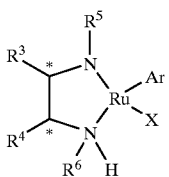

(II)

(wherein * represents an asymmetric carbon atom, $R^3$ and $R^4$ are the same or different and each represents an alkyl group or phenyl group or a cycloalkyl group which may have an alkyl group, or $R^3$ and $R^4$ may form an alicyclic ring unsubstituted or substituted by an alkyl group together with adjacent carbon atoms, $R^5$ represents methanesulfonyl group; trifluoromethanesulfonyl group; benzene sulfonyl group or naphthyl group which may be substituted by an alkyl group, an alkoxy group, or a halogen atom; camphorsulfonyl group; an alkoxycarbonyl group; or benzoyl group which may be substituted by an alkyl group, $R^6$ represents hydrogen atom or an alkyl group, Ar represents an aromatic compound which may be substituted by an alkyl group, and X represents a halogen atom), (2) the process for producing an optically active alcohol as described in above (1), wherein $R^1$ is a $C_1$–$C_7$ linear or branched perfluoroalkyl or perchloroalkyl group, (3) the process for producing an optically active alcohol as described in above (1), wherein $R^3$ and $R^4$ of the optically active ruthenium-diamine complex (II) are each phenyl group, $R^6$ is hydrogen atom, and X is chlorine atom, (4) the process for producing an optically active alcohol as described in above (1) or (2), wherein Ar of the optically active ruthenium-diamine complex (II) is p-cymene, benzene, or mesitylene, and (5) the process for producing an optically active alcohol as described in any one of above (1) to (4), wherein the reaction is conducted in the presence of a hydrogen-donating substance.

DETAILED DESCRIPTION OF THE INVENTION

In explanation of the β-keto ester to be used in the invention with reference to the general formula (I), $R^1$ in the formula is a $C_1$–$C_{10}$ linear or branched perfluoroalkyl or perchloroalkyl group, and more specifically, pentafluoroethyl group, heptafluoropropyl group, nonafluorobutyl group, undecafluoropentyl group, tridecafluorohexyl group, pentadecafluoroheptyl group, trifluoromethyl group and trichloromethyl group are mentioned.

Examples of $R^2$ specifically include $C_1$–$C_6$ alkyl group such as methyl group, ethyl group, n-propyl group, isopropyl group, n-butyl group, sec-butyl group, tert-butyl group, n-pentyl group, 2-pentyl group, 3-pentyl group, n-hexyl group, 2-hexyl group, and 3-hexyl group, and benzyl group which may have a substituent, such as benzyl group, p-methylbenzyl group, p-methoxybenzyl group, and p-nitrobenzyl group. Particularly, preferred are $C_1$–$C_4$ alkyl groups, i.e., methyl group, ethyl group, n-propyl group, isopropyl group, n-butyl group, sec-butyl group, and tert-butyl group.

In explanation of the optically active ruthenium-diamine complex to be used in the invention with reference to the general formula (II), $R^3$ and $R^4$ in the formula are the same or different and each is (1) an alkyl group or (2) phenyl group or a cycloalkyl group which may have an alkyl group, or (3) $R^3$ and $R^4$ may form an alicyclic ring unsubstituted or substituted by an alkyl group together with adjacent carbon atoms. More specifically, $R^3$ and $R^4$ each is an alkyl group, preferably a $C_1$–$C_4$ alkyl group, and may be a linear or branched alkyl group. Examples of $R^3$ and $R^4$ specifically include methyl group, ethyl group, n-propyl group, isopropyl group, n-butyl group, isobutyl group, sec-butyl group, and tert-butyl group. More preferred are methyl group, ethyl group, n-propyl group and isopropyl group.

In the case that $R^3$ and $R^4$ form an alicyclic ring unsubstituted or substituted by an alkyl group together with adjacent carbon atoms, the ring may be a five- to seven-membered ring, and the alkyl group by which the ring is substituted may be, for example, a $C_1$–$C_4$ alkyl group, specifically methyl group, ethyl group, n-propyl group, isopropyl group, n-butyl group, sec-butyl group, isobutyl, tert-butyl group, or the like. Particularly preferred is methyl group.

$R^3$ and $R^4$ in the case that $R^3$ and $R^4$ is phenyl group which may have an alkyl group specifically include phenyl, o-, m-, or p-tolyl group, and o-, m-, or p-anisyl group. More preferred specific example is the case that $R^3$ and $R^4$ each is phenyl group or that $R^3$ and $R^4$ represent tetramethylene group (—$(CH_2)_4$—) in combination.

$R^5$ represents (1) methanesulfonyl group, (2) trifluoromethanesulfonyl group, (3) benzene sulfonyl group or naphthyl group which may be substituted by an alkyl group (e.g., a $C_1$–$C_3$ alkyl group), an alkoxy group (e.g., a $C_1$–$C_3$ alkoxy group), or a halogen atom, (4) camphorsulfonyl group, (5) an alkoxycarbonyl group, or (6) benzoyl group which may be substituted by an alkyl group (e.g., a $C_1$–$C_4$ alkyl group).

$R^5$ as benzenesulfonyl group which may be (e.g., a $C_1$–$C_4$ alkyl group) substituted by a $C_1$–$C_3$ alkyl group, a $C_1$–$C_3$ alkoxy group, or a halogen atom is specifically benzenesulfonyl group, o-, m-, or p-toluenesulfonyl group, o-, m-, or p-ethylbenzenesulfonyl group, o-, m-, or p-isopropylbenzenesulfonyl group, o-, m-, or p-tert-butylbenzenesulfonyl group, o-, m-, or p-methoxybenzenesulfonyl group, o-, m-, or p-ethoxybenzenesulfonyl group, o-, m-, or p-chlorobenzenesulfonyl group, o-, m-, or p-fluorobenenesulfonyl group, 2,4,6-trimethylbenzenesulfonyl group, 2,4,6-triisopropylbenezenesulfonyl group, or the like, and more preferred is benzenesulfonyl group or p-toluenesulfonyl group.

$R^5$ as a $C_1$–$C_4$ alkoxycarbonyl group is specifically methoxycarbonyl group, ethoxycarbonyl group, isopropoxycarbonyl group, tert-butoxycarbonyl group, or the like, and more preferred is methoxycarbonyl group or tert-butoxycarbonyl group.

$R^5$ as benzoyl group which may be substituted by a $C_1$–$C_4$ alkyl group is specifically benzoyl group, o-, m-, or p-methylbenzoyl group, o-, m-, or p-ethylbenzoyl group, o-, m-, or p-isopropylbenzoyl group, o-, m-, or p-tert-butylbenzoyl group, or the like, and more preferred is benzoyl group or p-methylbenzoyl group.

In the most preferred specific examples, $R^5$ is methanesulfonyl group, trifluoromethanesulfonyl group, benzenesulfonyl group, or p-toluenesulfonyl group.

$R^6$ which represents hydrogen atom or a $C_1$–$C_4$ alkyl group is specifically hydrogen, methyl group, ethyl group, n-propyl group, isopropyl group, n-butyl group, sec-butyl group, tert-butyl group, or the like, and more preferred is hydrogen or methyl group.

Furthermore, the aromatic compound represented by Ar, which may be substituted by an alkyl group (preferably a $C_1$–$C_4$ alkyl group), in the optically active ruthenium-diamine complex (II) includes, for example, benzene, toluene, xylene, mesitylene, hexamethylbenzene, ethylbenzene, tert-butylbenzene, p-cymene, cumene, and the like. Preferred is benzene, mesitylene, or p-cymene.

The amount of the above optically active ruthenium-diamine complex in the invention varies depending on the size of the reaction vessel and economical efficiency, but the complex is used in a molar ratio of about 1/10 to 1/10000, preferably about 1/100 to 1/5000 relative to the substrate compound of the general formula (I).

In the invention, it is usually preferable to allow to exist a hydrogen-donating substance in the reaction system. The hydrogen-donating substance for use in the production of an optically active hydroxy compound by hydrogen-transfer type reduction in the invention is an organic or inorganic compound, which may be any compound as far as it can donate hydrogen in the reaction system through a thermal action or catalytic action.

The hydrogen-donating substance is not particularly limited to a specific kind, but preferred is formic acid or a salt thereof, e.g., a combination of formic acid and an amine, hydroquinone, phosphorous acid, or the like. Of these, preferred is formic acid or a combination of formic acid and an amine. The amine includes trimethylamine, triethylamine, and the like. In the case that formic acid or a combination of formic acid and an amine is used as a hydrogen source, a solvent may not be employed. In the reaction, any solvent can be employed unless it inhibits the reaction. As the solvent, specifically, use may be made of alcohol compounds such as methanol and ethanol; aromatic compounds such as toluene and xylene; aliphatic ester compounds such as methyl acetate, ethyl acetate, and butyl acetate; halogenated compounds such as dichloromethane; aliphatic compounds such as hexane and heptane; ether compounds such as tetrahydrofuran and diethyl ether; other organic compounds such as dimethyl sulfoxide, N,N-dimethylformamide, and acetonitrile.

The reaction temperature may be about –20 to about 100° C., and in view of the economic efficiency, the reaction can be conducted more practically in the vicinity of room temperature, i.e., about 25 to about 40° C.

The reaction period of time varies depending on the reaction conditions such as substrate concentration, catalyst concentration, and temperature, but the reaction generally finishes within several minutes to 100 hours.

According to the invention, the compound represented by the general formula (III) is obtained in high optical purity. For example, in the case that the compound of the formula (I) is shown by $CF_3$—CO—$CH_2$—$COOR^2$, and the compound of the formula (II) has a configuration of (R,R), the aimed product represented by the formula (III) is obtained as a (R)-(+)-body.

The following will explain the invention in further detail with reference to Examples, but the invention is not limited to these Examples.

The optically active ruthenium-diamine complex used in Examples was prepared by the method described in JP-A-10-130289 or J. Am. Chem. Soc., Vol. 118, pp. 2521–2522 (1996).

Moreover, Commercial products (products manufactured by Tokyo Kasei Kogyo Co., Ltd.) were used as methyl 4,4,4-trifluoro-3-oxobutanoate, ethyl 4,4,4-trifluoro-3-oxobutanoate, isopropyl 4,4,4-trifluoro-3-oxobutanoate, and ethyl 4,4,4-trichloro-3-oxobutanoate used in Examples.

Methyl 3-oxo-4,4,5,5,6,6,7,7,8,8,9,9,10,10,10-pentadecafluorodecanoate used in the Example was prepared by the procedure described in the literature (J. Fluorine Chem., Vol. 20, 187–202 (1982)).

Furthermore, the chemical purity, conversion, and optical purity were determined by the apparatus and methods shown in the following.

Additionally, in Examples and Referential Examples, Ts represents toluenesulfonyl group.

Chemical Purity and Conversion:

| | |
|---|---|
| Gas Chromatograph: | GC 353B (manufactured by GL Science Inc.) |
| Column: | TC-5HT (0.25 mm × 30 m) (manufactured by GL Science Inc.) |
| Injection Temperature: | 130° C. |
| Detector Temperature: | 150° C. |
| Initial Temperature: | 50° C. |
| Final Temperature: | 120° C. |
| Rate: | 3.0° C./minute |
| Optical Purity: | |
| Gas Chromatograph: | 5890 SERIES II (manufactured by HEWLETT PACKARD Co.) |
| Column: | ChiralDex-B-TA (0.25 mm × 30 m) (manufactured by Astec Inc.) |
| Injection Temperature: | 180° C. |
| Detector Temperature: | 200° C. |
| Initial Temperature: | 50° C. |
| Final Temperature: | 120° C. |
| Rate: | 3.0° C./minute |

REFERENTIAL EXAMPLE 1

To a solution of 5 mL of a mixture of formic acid-triethylamine (5:2 in molar ratio) and 11 mg of an optically active ruthenium-diamine complex, RuCl[(1R,2R)-p-TsNHCH($C_6H_5$)CH($C_6H_5$)$NH_2$] (p-cymene) dissolved in 5 mL of tetrahydrofuran was added 1.00 g of methyl acetoacetate, followed by stirring at 35° C. for 21 hours. Thereafter, the reaction mixture was analyzed on the gas chromatograph, but proceeding of any reaction was not observed.

REFERENTIAL EXAMPLE 2

To a solution of 5 mL of a mixture of formic acid-triethylamine (5:2 in molar ratio) and 7.7 mg of an optically active ruthenium-diamine complex, RuCl[(1R,2R)-p-TsNHCH($C_6H_5$)CH($C_6H_5$)$NH_2$] (p-cymene) dissolved in 5 mL of tetrahydrofuran was added 1.00 g of ethyl 4-chloroacetoacetate, followed by stirring at 35° C. for 19.5 hours. Thereafter, the reaction mixture was analyzed on the gas chromatograph, and the conversion was found to be 52%.

EXAMPLE 1

A solution of 50 mL of a mixture of formic acid-triethylamine (5:2 in molar ratio) and 70.1 mg of RuCl[(1R,2R)-p-TsNHCH($C_6H_5$)CH($C_6H_5$)$NH_2$] (p-cymene) dissolved in 25 mL of tetrahydrofuran was stirred at 35° C., and a solution of 10.0 g of ethyl 4,4,4-trifluoro-3-oxobutanoate dissolved in 25 mL of tetrahydrofuran was added thereto over a period of 30 minutes. The reaction mixture was stirred at the same temperature for 21 hours and the conversion into the hydroxy compound was found to be 100%. After the reaction mixture was concentrated under reduced pressure using an evaporator, 20 mL of water and 40 mL of ethyl acetate were added to the resulting concentrate and then a saturated sodium carbonate aqueous solution was added thereto under stirring until the pH became 7 or higher. After the separation of the ethyl acetate layer, the water layer was further extracted with 25 mL of ethyl acetate. Then, the ethyl acetate layer was combined with the previous ethyl acetate layer and the combined layer was concentrated. The resulting concentrate was distilled under reduced pressure (88–89° C./2660 Pa) to obtain 8.96 g of optically active ethyl 4,4,4-trifluoro-3-hydroxybutanoate (yield 88.6%). Upon the measurement under the above conditions, the optical purity of the resulting optically active ethyl 4,4,4-trifluoro-3-hydroxybutanoate was found to be 94.2% e.e.

EXAMPLE 2

To 10 mL of acetonitrile were added 5 mL of a mixture of formic acid-triethylamine (5:2 in molar ratio), 7 mg of RuCl[(1R,2R)-p-TsNHCH($C_6H_5$)CH($C_6H_5$)$NH_2$] (p-cymene), and 1.0 g of ethyl 4,4,4-trifluoro-3-oxobutanoate, and the whole was stirred at 35° C. for 15 hours, followed by concentration under reduced pressure using an evaporator. To the resulting concentrate were added 10 mL of water and 10 mL of ethyl acetate, and then a saturated sodium carbonate aqueous solution was added thereto under stirring until the pH became 7 or higher. The ethyl acetate layer separated from the aqueous layer was concentrated to obtain optically active ethyl 4,4,4-trifluoro-3-hydroxybutanoate. Upon the measurement under the above conditions, the optical purity and conversion were found to be 95.0% e.e. and 99.9%, respectively.

EXAMPLE 3

To 10 mL of i-propanol were added 5 mL of a mixture of formic acid-triethylamine (5:2 in molar ratio), 7 mg of RuCl[(1R,2R)-p-TsNHCH($C_6H_5$)CH($C_6H_5$)$NH_2$] (p-cymene), and 1.0 g of ethyl 4,4,4-trifluoro-3-oxobutanoate, and the whole was stirred at 35° C. for 15 hours, followed by concentration under reduced pressure using an evaporator. To the resulting concentrate were added 10 mL of water and 10 mL of ethyl acetate, and then a saturated sodium carbonate aqueous solution was added thereto under stirring until the pH became 7 or higher. The ethyl acetate layer separated from the aqueous layer was concentrated to obtain optically active ethyl 4,4,4-trifluoro-3-hydroxybutanoate. Upon the measurement under the above conditions, the optical purity and conversion were found to be 94.8% e.e. and 99.9%, respectively.

EXAMPLE 4

To 6 mL of methanol were added 5 mL of a mixture of formic acid-triethylamine (5:2 in molar ratio), 1.0 g of methyl 4,4,4-trifluoro-3-oxobutanoate, and 7.5 mg of RuCl[(1R,2R)-p-TsNHCH($C_6H_5$)CH($C_6H_5$)$NH_2$] (p-cymene), and the whole was stirred at 35° C. for 15 hours, followed by concentration under reduced pressure using an evaporator. To the resulting concentrate were added 10 mL of water and 10 mL of ethyl acetate, and then a saturated sodium carbonate aqueous solution was added thereto under stirring until the pH became 7 or higher. The ethyl acetate layer separated from the aqueous layer was concentrated to obtain optically active methyl 4,4,4-trifluoro-3-hydroxybutanoate. Upon the measurement under the above conditions, the optical purity and conversion were found to be 94.6% e.e. and 100%, respectively.

EXAMPLE 5

Into 6 mL of tetrahydrofuran were dissolved 7.5 mg of RuCl[(1R,2R)-p-TsNHCH($C_6H_5$)CH($C_6H_5$)$NH_2$] (p-cymene), 5 mL of a mixture of formic acid-triethylamine (5:2 in molar ratio), 1.0 g of methyl 4,4,4-trifluoro-3-oxobutanoate, and the whole was stirred at 35° C. for 15 hours, followed by concentration under reduced pressure using an evaporator. To the resulting concentrate were added 10 mL of water and 10 mL of ethyl acetate, and then a saturated sodium carbonate aqueous solution was added thereto under stirring until the pH became 7 or higher. The ethyl acetate layer separated from the aqueous layer was concentrated to obtain optically active methyl 4,4,4-trifluoro-3-hydroxybutanoate. Upon the measurement under the above conditions, the optical purity and conversion were found to be 96.4% e.e. and 100%, respectively.

EXAMPLE 6

The reaction was conducted under the same reaction conditions as in Example 5 with the exception that the solvent, tetrahydrofuran used in Example 5 was changed to toluene. The optical purity and conversion were found to be 96.1% e.e. and 74.5%, respectively.

EXAMPLE 7

Into 6 mL of tetrahydrofuran were dissolved 6.4 mg of RuCl[(1R,2R)-p-TsNHCH($C_6H_5$)CH($C_6H_5$)$NH_2$] (p-cymene), 5 mL of a mixture of formic acid-triethylamine (5:2 in molar ratio), 1.0 g of isopropyl 4,4,4-trifluoro-3-oxobutanoate, and the whole was stirred at 35° C. for 15 hours, followed by concentration under reduced pressure using an evaporator. To the resulting concentrate were added 10 mL of water and 10 mL of ethyl acetate, and then a saturated sodium carbonate aqueous solution was added thereto under stirring until the pH became 7 or higher. The ethyl acetate layer separated from the aqueous layer was concentrated to obtain optically active isopropyl 4,4,4-trifluoro-3-hydroxybutanoate. Upon the measurement under the above conditions, the optical purity and conversion were found to be 96.2% e.e. and 100%, respectively.

EXAMPLE 8

The reaction was conducted under the same reaction conditions as in Example 7 with the exception that the solvent, tetrahydrofuran used in Example 7 was changed to ethyl acetate. The optical purity and conversion were found to be 96.1% e.e. and 100%, respectively.

EXAMPLE 9

The reaction was conducted under the same reaction conditions as in Example 7 with the exception that the solvent, tetrahydrofuran used in Example 7 was changed to methanol. The optical purity and conversion were found to be 95.9% e.e. and 99.8%, respectively.

EXAMPLE 10

The reaction was conducted under the same reaction conditions as in Example 7 with the exception that 1.0 g of ethyl 4,4,4-trichloro-3-oxobutanoate was used instead of 1.0 g of isopropyl 4,4,4-trifluoro-3-oxobutanoate used in Example 7. The optical purity and conversion were found to be 97.2% e.e. and 95.2%, respectively.

EXAMPLE 11

To 1.25 mL of tetrahydrofuran were added 2.5 mL of a mixture of formic acid-triethylamine (5:2 in molar ratio), 6.8 mg of $RuCl[(1R,2R)\text{-}p\text{-}TsNHCH(C_6H_5)CH(C_6H_5)NH_2]$ (p-cymene), and 0.50 g of methyl 3-oxo-4,4,5,5,6,6,7,7,8,8,9,9,10,10,10-pentadecafluorodecanoate, and the whole was stirred at 35° C. for 17 hours. Thereafter, the reaction mixture was analyzed on the gas chromatography, and the conversion was found to be 98.8%. After the reaction mixture was concentrated undere reduced pressure using an evaporator, 1 mL of water and 2 mL of diethyl ether were added to the resulting concentrate and then a saturated sodium carbonate aqueous solution was added thereto under stirring until the pH became 7 or higher. After the separation of the diethyl ether layer, the water layer was extracted with 5 mL of diethyl ether. Then, the diethyl ether layer was combined with the previous diethyl ether layer and the combined diethyl ether layer was concentrated. The resulting concentrate was distilled under reduced pressure (65° C./53 Pa) to obtain 0.22 g of optically active methyl 3-hydroxy-4,4,5,5,6,6,7,7,8,8,9,9,10,10,10-pentadecafluorodecanoate (yield 43.8%). Upon the measurement under above conditions, the optical purity of the trifluoroacetate of the optically active methyl 3-hydroxy-4,4,5,5,6,6,7,7,8,8,9,9,10,10,10-pentadecafluorodecanoate was found to be 91.6% e.e. $^1$H-NMR (500 MHz: CDCl$_3$) δ=2.6–2.75 (2H, m), 3.68 (3H, s), 3.78 (1H, br s), 4.5–4.65 (1H, m).

According to the process of the invention for producing an optically active alcohol, an optically active alcohol having a high optical purity can be conveniently obtained in high yields, so that the process is very useful in the fields of medicines and functional materials.

While the invention has been described in detail and with reference to specific embodiments thereof, it will be apparent to one skilled in the art that various changes and modifications can be made therein without departing from the scope thereof.

This application is based on Japanese patent applications No. 2001-150012 filed May 18, 2001 and No. 2002-082865 filed Mar. 25, 2002, the entire contents thereof being hereby incorporated by reference.

What is claimed is:

1. A process for producing an optically active alcohol represented by the general formula (III):

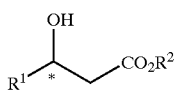

(III)

(wherein * represents an asymmetric carbon atom, $R^1$ represents a $C_1$–$C_{10}$ linear or branched perfluoroalkyl or perchloroalkyl group and $R^2$ represents a $C_1$–$C_8$ lower alkyl group or benzyl group which may have a substituent), which comprises a step of subjecting a β-keto ester represented by the general formula (I):

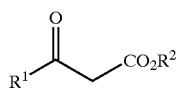

(I)

(wherein $R^1$ and $R^2$ each has the same meaning as described above) to a hydrogen-transfer reaction in the presence of an optically active ruthenium-diamine complex represented by the general formula (II):

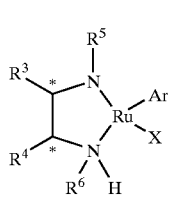

(II)

(wherein * represents an asymmetric carbon atom, $R^3$ and $R^4$ are the same or different and each represents an alkyl group or phenyl group or a cycloalkyl group which may have an alkyl group, or $R^3$ and $R^4$ may form an alicyclic ring unsubstituted or substituted by an alkyl group together with adjacent carbon atoms, $R^5$ represents methanesulfonyl group; trifluoromethanesulfonyl group; benzene sulfonyl group or naphthyl group which may be substituted by an alkyl group, an alkoxy group, or a halogen atom; camphorsulfonyl group; an alkoxycarbonyl group; or benzoyl group which may be substituted by an alkyl group, $R^6$ represents hydrogen atom or an alkyl group, Ar represents an aromatic compound which may be substituted by an alkyl group, and X represents a halogen atom).

2. The process for producing an optically active alcohol according to claim 1, wherein $R^1$ is a $C_1$–$C_7$ linear or branched perfluoroalkyl or perchloroalkyl group.

3. The process for producing an optically active alcohol according to claim 1, wherein $R^3$ and $R^4$ of the optically active ruthenium-diamine complex (II) are each phenyl group, $R^6$ is hydrogen atom, and X is chlorine atom.

4. The process for producing an optically active alcohol according to claim 2, wherein $R^3$ and $R^4$ of the optically active ruthenium-diamine complex (II) are each phenyl group, $R^6$ is hydrogen atom, and X is chlorine atom.

5. The process for producing an optically active alcohol according to claim 1, wherein Ar of the optically active ruthenium-diamine complex (II) is p-cymene, benzene, or mesitylene.

6. The process for producing an optically active alcohol according to claim 2, wherein Ar of the optically active ruthenium-diamine complex (II) is p-cymene, benzene, or mesitylene.

7. The process for producing an optically active alcohol according to any one of claims 1 to 6, wherein the reaction is conducted in the presence of a hydrogen-donating substance.

* * * * *